United States Patent

Lehnen et al.

[11] Patent Number: 5,982,493
[45] Date of Patent: Nov. 9, 1999

[54] APPARATUS AND METHOD FOR ACQUIRING MULTIPLE IMAGES

[75] Inventors: David Charles Lehnen; Christopher John LeBeau, both of Tempe, Ariz.

[73] Assignee: Motorola, Inc., Schaumburg, Ill.

[21] Appl. No.: 09/089,592

[22] Filed: Jun. 2, 1998

[51] Int. Cl.$^6$ ............ G01B 11/14; G01B 11/24; G01B 11/00; G01N 21/00

[52] U.S. Cl. .......... 356/375; 356/376; 356/372; 356/237.1; 250/559.23; 250/559.31

[58] Field of Search ................ 356/236, 237, 356/399, 435, 375, 376, 372, 237.1; 250/559.23, 559.31

[56] References Cited

U.S. PATENT DOCUMENTS

| | | | |
|---|---|---|---|
| 4,645,924 | 2/1987 | Suzuki et al. | 250/236 |
| 4,884,890 | 12/1989 | Coates | 356/237 |
| 5,197,105 | 3/1993 | Uemura et al. | 356/237 |
| 5,404,277 | 4/1995 | Lindblad | 362/31 |
| 5,440,391 | 8/1995 | Smeyers et al. | 356/375 |
| 5,485,318 | 1/1996 | Lebby et al. | 359/811 |
| 5,546,888 | 8/1996 | Skiver et al. | 116/286 |
| 5,617,209 | 4/1997 | Svetkoff et al. | 356/376 |
| 5,654,800 | 8/1997 | Svetkoff et al. | 356/376 |
| 5,703,713 | 12/1997 | Leong | 359/352 |
| 5,706,091 | 1/1998 | Shiraishi | 356/399 |
| 5,714,762 | 2/1998 | Li et al. | 250/559.2 |

*Primary Examiner*—F. L. Evans
*Assistant Examiner*—Roy M. Punnoose
*Attorney, Agent, or Firm*—Anthony M. Martinez

[57] ABSTRACT

An image station (40) includes multiple light sources (43, 45, 47, 49) emitting lights of different colors to illuminate an object (41) from different directions, thereby forming multiple images of the object (41). Dichroic filters (54, 56, 58) separate lights of different colors from each other. Lights of different colors form images of the object (41) in corresponding cameras (53, 55, 57, 59) simultaneously.

14 Claims, 1 Drawing Sheet

10

40

APPARATUS AND METHOD FOR ACQUIRING MULTIPLE IMAGES

BACKGROUND OF THE INVENTION

The present invention relates, in general, to forming optical images and, more particularly, to forming multiple images of an object.

Typically, work pieces such as semiconductor devices are visually inspected to insure that they meet design specifications for parameters such as lead coplanarity, lead length, lead straightness, mark inspection, surface inspection, lead pitch, etc. A semiconductor device under inspection is usually placed on a visual inspection station. Using either front lighting or back lighting technique, images of the device are formed and analyzed using a vision computer.

Certain types of inspections require multiple views of the device. This can be achieved using multiple illuminations. Different illuminations providing different views sometimes interfere with each other. For example, the illuminations for dark field image and bright field image interfere with each other. Multiple back lighting illuminations used for generating multiple shadow images of the device also interfere with each other. Illuminating the device with one light beam at a time and forming multiple images of the device sequentially will avoid the interference. This requires the device to be stationary over the whole time interval of changing illuminations and acquiring multiple images. An inspection process using such techniques is complicated and time consuming.

Accordingly, it would be advantageous to have an apparatus and a method for acquiring multiple images of an object. It is desirable for the apparatus to be simple and inexpensive. It is also desirable for the method to be time efficient. It would be of further advantage for the apparatus and the method to be compatible with existing equipment and inspection process.

It should be understood that for simplicity and clarity of illustration, the figures are not necessarily drawn to scale.

DETAILED DESCRIPTION OF THE DRAWINGS

Generally, the present invention provides an apparatus and a method for acquiring multiple images of an object. The images can be front light images or back light images. The multiple images provides multiple views of the object. In accordance with the present invention, multiple lights of different frequencies illuminate the object from different directions, thereby providing different views of the object. Multiple photosensors such as, for example, cameras sense the multiple lights to acquire multiple images of the object. Each photosensor senses a light of a particular wavelength range or frequency band and acquires an image of a particular view. This multiple spectrum illumination technique substantially eliminates the interference between different illuminations that would adversely affect the inspection process of the device.

Figure 1:
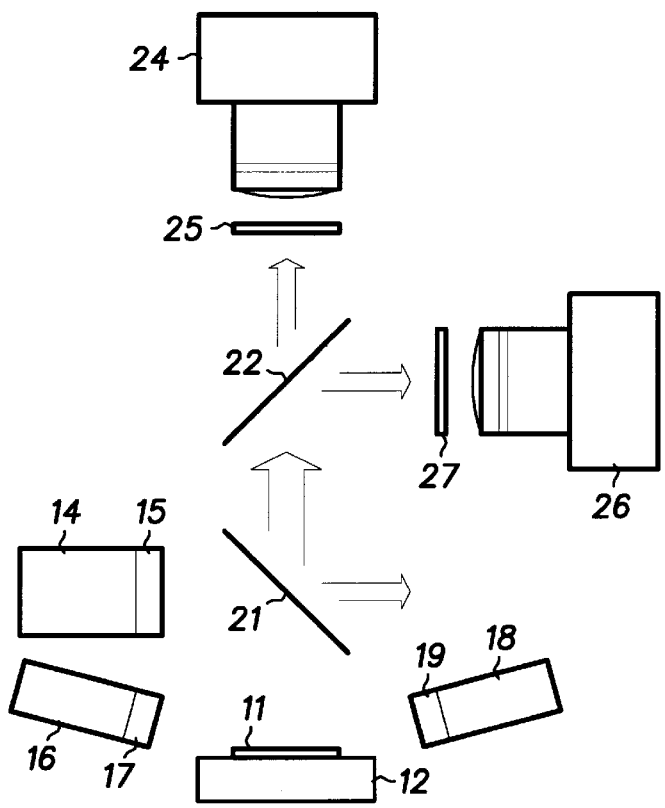
FIG. 1 schematically illustrates a multiple image acquisition apparatus in accordance with a first embodiment of the present invention.

FIG. 1 schematically illustrates a multiple image acquisition apparatus 10 in accordance with a first embodiment of the present invention. Apparatus 10 is used to form multiple images of an object 11 and visually inspect object 11. By way of example, object 11 is a semiconductor device and apparatus 10 visually inspects surface features of device 11. Apparatus 10 is also referred to as an image station, a visual inspection station, or a surface inspection station. Apparatus 10 includes a platform 12 and light sources 14, 16, and 18. Platform 12 supports device 11. Light source 14 emits light having a wavelength range different from that of light emitted by light sources 16 and 18. Apparatus 10 also includes beam splitters 21 and 22, photosensors, e.g., cameras 24 and 26, and filters 25 and 27.

By way of example, light source 14 includes a high pass filter 15 and emits light of a short wavelength or high frequency, and each of light sources 16 and 18 includes low pass filters 17 and 19, respectively, and emits light of a long wavelength or low frequency. More particularly, light source 14 emits a blue light having a wavelength range between approximately 450 nanometers (nm) and approximately 500 nm or a frequency range between approximately 600 terahertz (THz) and approximately 670 THz, and light sources 16 and 18 emit a red light having a wavelength range between approximately 650 nm and approximately 700 nm or a frequency range between approximately 425 THz and approximately 460 THz.

Beam splitter 21 functions as a deflector that reflects the blue light emitted by light source 14 and generates a deflected light. It should be noted that a portion of the blue light emitted from light source 14 transmits through beam splitter 21. This portion of the blue light does not contribute to the process of forming images of device 11. The deflected blue light illumines device 11 from a direction substantially perpendicular to a surface of device 11 and generates a bright field image of the surface. When viewing the bright field image from a direction substantially perpendicular to the surface, smooth portions of the surface are brighter than coarse or rough portions of the surface that have features such as, for example, cracks, voids, pits, ridges, protuberances, etc. The red light emitted from light sources 16 and 18 illumines device 11 from directions oblique to the surface of device 11 and generates a dark field image of the surface. When viewing the dark field image from a direction substantially perpendicular to the surface, the smooth portions of the surface appear to be darker than the coarse portions of the surface. Analyzing bright field image and dark field image is a simple and efficient way of inspecting the surface of device 11.

The blue bright field image beam and the red dark field image beam propagate toward beam splitter 21, which reflects a portion of the image beams. The reflected portion of the image beams does not contribute to the image formation in cameras 24 and 26. The remaining portion of the image beams transmits through beam splitter 21 and propagates toward beam splitter 22 located in a light path between beam splitter 21 and camera 24. A portion of the image beams reaching beam splitter 22 transmits through beam splitter 22 and propagates toward camera 24. Filter 25 is a high pass filter that filters out light of long wavelength or low frequency. It blocks the red dark field image beam from reaching camera 24. The blue bright field image beam transmitted through beam splitter 22 reaches camera 24 and forms a bright field image of device 11 therein. Another portion of the image beams reaching beam splitter 22 is reflected by beam splitter 22 and propagates toward camera 26. Filter 27 is a low pass filter that filters out light of short wavelength or high frequency. It blocks the blue bright field image beam from reaching camera 26. The red dark field image beam reflected by beam splitter 22 reaches camera 26 and forms a dark field image of device 11 therein. Thus, multiple image acquisition apparatus 10 has acquired two images of semiconductor device 11 substantially simultaneously. A vision computer (not shown) coupled to cameras 24 and 26 analyzes the two images and perform a visual inspection of semiconductor device 11.

It should be noted that FIG. 1 only shows those features of apparatus 10 which are relevant to its optical operation. It should also be understood that the structure of apparatus 10 is not limited to being that described hereinbefore. For example, one of light sources 16 and 18 is optional. A single light source, e.g., light source 16, illumining device 11 from a direction oblique to the surface of device 11 can provide a dark field image thereof. On the other hand, apparatus 10 can include more than two light sources for forming a dark field image of device 11. Apparatus 10 can also include a ring structured light source for illumining device 11 and forming a dark field image thereof. High pass filter 15 and low pass filters 17 and 19 are optional in apparatus 10. In an alternative embodiment, apparatus 10 does not include high pass filter 15 and low pass filters 17 and 19, light source 14 is replaced with a narrow bandwidth or monochromatic blue light source, and light sources 16 and 18 are replaced with narrow bandwidth or monochromatic red light sources. In another alternative embodiment, beam splitter 22 is replaced with a dichroic filter that transmits high frequency light and reflects low frequency light. The blue bright field image beam reaching the dichroic filter substantially transmits therethrough, and the red dark field image beam reaching the dichroic filter is substantially reflected thereby. The dichroic filter eliminates the need for high pass filter 25 in front of camera 24 and low pass filter 27 in front of camera 26. In yet another embodiment, the bright field and dark field illuminations of device 11 are provided by a single light source (not shown) emitting a wide bandwidth light, e.g., a strobe light emitting white light. The wide bandwidth light emitted by the single light source transmits through at least two separate light paths to illumine device 11 from at least two different directions. The light paths can be established using lenses, mirrors, optical fibers, or the like. Different filters, e.g., high pass filter 15 and low pass filters 17 and 19, are incorporated in different light paths to generate light beams in different wavelength ranges or different frequency bands which illumine device 11 from different directions.

Figure 2:
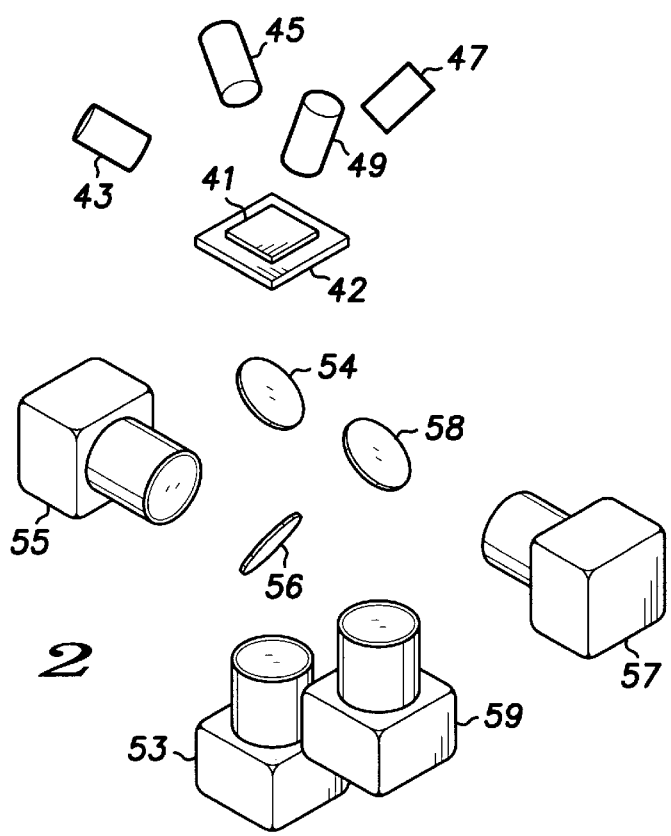
FIG. 2 schematically illustrates an image station in accordance with a second embodiment of the present invention.

FIG. 2 schematically illustrates an image station 40 in accordance with a second embodiment of the present invention. Through multi-spectral illumination, image station 40 forms multiple images of an object 41 and visually inspects object 41. Image station 40 is also referred to as a multiple image acquisition apparatus or an inspection station. By way of example, object 41 is a semiconductor device. Image station 40 includes a platform 42 and narrow bandwidth or monochromatic light sources 43, 45, 47, and 49. Platform 42 supports semiconductor device 41. Platform 42 is a translucent platform or a translucent plate made of a material such as, for example, translucent plastic, ground glass, or the like. Light sources 43, 45, 47, and 49 illuminate device 41 from different directions with lights in different wavelength ranges or at different frequencies from each other. In other words, light sources 43, 45, 47, and 49 emit light in different colors or different spectrum bands. By way of example, light source 43 emits a blue light having a frequency of approximately 650 THz, light source 45 emits a green light having a frequency of approximately 575 THz, light source 47 emits a yellow light having a frequency of approximately 500 THz, and light source 49 emits a red light having a frequency of approximately 425 THz.

Image station 40 also includes dichroic beam splitters or dichroic filters 54, 56, and 58, and cameras 53, 55, 57, and 59. Dichroic filter 54 is in a light path between platform 42 and camera 53. Dichroic filter 56 is in a light path between dichroic filter 54 and camera 53. Dichroic filter 58 is in a light path between dichroic filter 54 and camera 57. By way of example, dichroic filter 54 substantially transmits and reflects lights having frequencies higher and lower, respectively, than approximately 550 THz, dichroic filter 56 substantially transmits and reflects lights having frequencies higher and lower, respectively, than approximately 600 THz, and dichroic filter 58 substantially transmits and reflects lights having frequencies higher and lower, respectively, than approximately 450 THz.

In a process of inspecting device 41, light source 43, 45, 47, and 49 illuminate device 41 and generate four shadow images of device 41 on translucent platform 42. Four shadow image light beams having different directions of views and different colors from each other propagate from translucent platform 42 toward dichroic filter 54. The blue and green image light beams have frequencies higher than 550 THz, transmit through dichroic filter 54, and propagate toward dichroic filter 56. The yellow and red image light beams have frequencies lower than 550 THz, are reflected by dichroic filter 54, and propagate toward dichroic filter 58. Dichroic filter 56 transmits the blue image light beam which has a frequency higher than 600 THz and reflects the green image light beam which has a frequency lower than 600 THz. After transmitting through dichroic filter 56, the blue image light beam propagates toward camera 53 and forms a first shadow image of device 11 therein. After being reflected by dichroic filter 56, the green image light beam propagates toward camera 55 and forms a second shadow image of device 11 therein. Dichroic filter 58 transmits the yellow image light beam which has a frequency higher than 450 THz and reflects the red image light beam which has a frequency lower than 450 THz. After transmitting through dichroic filter 58, the yellow image light beam propagates toward camera 57 and forms a third shadow image of device 11 therein. After being reflected by dichroic filter 58, the red image light beam propagates toward camera 59 and forms a fourth shadow image of device 11 therein. Thus, image station 40 has acquired four shadow images of semiconductor device 41 substantially simultaneously. A vision computer (not shown) coupled to cameras 53, 55, 57, and 59 analyzes the four shadow images and inspects semiconductor device 41 to ensure that its parameters such as lead coplanarity, lead length, lead straightness, mark inspection, surface inspection, lead pitch, etc. meet predetermined design specifications. If they do not meet, device 41 may be rejected.

It should be noted that FIG. 2 only shows those features which are relevant to the optical operation of image station 40. It should also be understood that the structure and operation of image station 40 are not limited to being those described hereinbefore. In an alternative embodiment, light source 43, 45, 47, and 49 are replaced with light source emitting white light, and image station 40 include four filters (not shown), one in a light path between each of respective light sources 43, 45, 47, and 49 and device 41. In an another alternative embodiment, dichroic filters are replaced with ordinary beam splitters, and image station 40 include four filters (not shown), one in front of each of cameras 53, 55, 57, and 59. In yet another embodiment, image station 40 does not include light sources 43, 45, 47, and 49, and the multiple spectrum illumination of device 41 is provided by a single light source (not shown) emitting a wide bandwidth light, e.g., a strobe light emitting white light. The wide bandwidth light emitted by the single light source transmits through four separate light paths to illuminate device 41 from four different directions. The light paths can be established using lenses, mirrors, optical fibers, or the like. Four different filters are incorporated in the four light paths to generate four light beams in four different wavelength ranges or different frequency bands illuminating device 41 from four different directions.

By now it should be appreciated that an apparatus and a method for acquiring multiple images of an object have been provided. In accordance with the present invention, lights of different frequency bands illuminate the object from different directions, thereby providing different views of the object. Photosensors sense the lights to substantially simultaneously acquire multiple images of the object. Each photosensor senses a light of a particular frequency band and acquires an image of a particular view. This multiple spectrum illumination technique substantially eliminates the interference between different illuminations that would otherwise adversely affects the inspection process of the device. The apparatus of the present invention is simple and inexpensive. The process of the present invention is time efficient. In addition, the apparatus and the method are compatible with existing equipment and inspection process.

While specific embodiments of the present invention have been shown and described, further modifications and improvements will occur to those skilled in the art. It is understood that the present invention is not limited to the particular forms shown and it is intended for the appended claims to cover all modifications of the invention which fall within the true spirit and scope of the present invention. More particularly, the colors of the light described hereinbefore are only examples. They are not intended as an exhaustive enumeration of light bands which can be used in practicing the present invention. Further, the image acquisition process of the present invention is not limited to using visible light. Electromagnetic waves in other frequency bands such as, for example, infrared, ultraviolet, X-ray, etc. can also be used in forming multiple images in accordance with the present invention.

What is claimed is:

1. An image station for generating and acquiring shadow images of an object, comprising:
   a translucent platform, wherein the object is placed over the translucent platform;
   a first light source emitting a first light having a first frequency for illuminating the object and generating a first shadow image of the object on the translucent platform;
   a second light source emitting a second light having a second frequency for illuminating the object and generating a second shadow image of the object on the translucent platform;
   a first photosensor for receiving the first shadow image; and
   a second photosensor for receiving the second shadow image, wherein the first and second shadow images are received substantially simultaneously by the first and second photosensors and wherein the image station analyzes the first and second shadow images for inspection of the object to ensure that parameters of the object meet predetermined design specifications.

2. The image station of claim 1, further comprising a first dichroic filter in a light path between the translucent platform and the first photosensor.

3. The image station of claim 2, wherein the first dichroic filter substantially transmit the first shadow image and substantially reflects the second shadow image.

4. The image station of claim 1, further comprising:
   a third light source emitting a third light having a third frequency for illuminating the object and generating a third shadow image of the object on the translucent platform; and
   a third photosensor for receiving the third shadow image.

5. The image station of claim 4, further comprising:
   a first dichroic filter in a light path between the translucent platform and the first photosensor; and
   a second dichroic filter in a light path between the first dichroic filter and the first photosensor.

6. The image station of claim 5, wherein the first dichroic filter substantially transmits the first and second shadow images and substantially reflects the third shadow image and wherein the second dichroic filter substantially transmits the first shadow image and substantially reflects the second shadow image.

7. The image station of claim 5, further comprising:
   a fourth light source emitting a fourth light having a fourth frequency for illuminating the object and generating a fourth shadow image of the object on the translucent platform; and
   a fourth photosensor for receiving the fourth shadow image.

8. The image station of claim 7, further comprising a third dichroic filter in a light path between the first dichroic filter and the third photosensor.

9. The image station of claim 8,
   wherein the first dichroic filter substantially transmits the first and second shadow images and substantially reflects the third shadow image;
   wherein the second dichroic filter substantially transmits the first shadow image and substantially reflects the second shadow image; and
   wherein the third dichroic filter substantially transmits the third shadow image and substantially reflects the fourth shadow image.

10. The image station of claim 7, wherein the third light is yellow light and the third frequency is approximately 500 terahertz (THz) and wherein the fourth light is red light and the fourth frequency is approximately 425 THz.

11. The image station of claim 1, wherein the first light is blue light and the first frequency is approximately 650 terahertz (THz) and wherein the second light is green light and the second frequency is approximately 575 THz.

12. The image station of claim 1, wherein the object is between the translucent platform and the first and second light sources for generating the first and second shadow images, and wherein the translucent platform is between the object and the first and second photosensors for receiving the first and second shadow images.

13. A method for acquiring multiple shadow images of an object, comprising the steps of:
   illuminating the object with a first light having a first frequency to generate a first shadow image beam of the object on a translucent plate;

illuminating the object with a second light having a second frequency to generate a second shadow image beam of the object on the translucent plate;

receiving the first shadow image beam to acquire a first image of the object; and receiving the second shadow image beam to acquire a second image of the object, wherein the first shadow image beam and the second shadow image beam are received substantially simultaneously.

14. The method of claim 13, further comprising the steps of:

transmitting the first shadow image beam through a first dichroic beam splitter; and reflecting the second shadow image beam using the dichroic beam splitter.

* * * * *